(12) United States Patent
Ma et al.

(10) Patent No.: US 9,029,285 B2
(45) Date of Patent: May 12, 2015

(54) CATALYST FOR HYDROGENATION OF OXALIC ESTER TO ETHANOL, METHOD OF PREPARING THE CATALYST, AND METHOD OF USING THE SAME

(71) Applicant: Tianjin University, Tianjin (CN)

(72) Inventors: Xinbin Ma, Tianjin (CN); Jing Lv, Tianjin (CN); Yujun Zhao, Tianjin (CN); Shengping Wang, Tianjin (CN); Jinlong Gong, Tianjin (CN); Baowei Wang, Tianjin (CN); Zhenhua Li, Tianjin (CN); Yan Xu, Tianjin (CN)

(73) Assignee: Tianjin University, Tianjin (CN)

( * ) Notice: Subject to any disclaimer, the term of this patent is extended or adjusted under 35 U.S.C. 154(b) by 171 days.

(21) Appl. No.: 13/904,009

(22) Filed: May 28, 2013

(65) Prior Publication Data
US 2013/0261350 A1    Oct. 3, 2013

Related U.S. Application Data

(63) Continuation-in-part of application No. PCT/CN2012/075110, filed on May 7, 2012.

(51) Int. Cl.
| | | |
|---|---|---|
| *B01J 23/72* | (2006.01) | |
| *B01J 23/755* | (2006.01) | |
| *B01J 21/14* | (2006.01) | |
| *B01J 23/83* | (2006.01) | |
| *C07C 29/149* | (2006.01) | |
| *B01J 23/889* | (2006.01) | |
| *B01J 23/78* | (2006.01) | |
| *B01J 23/80* | (2006.01) | |
| *B01J 23/887* | (2006.01) | |

(52) U.S. Cl.
CPC ....... *B01J 23/83* (2013.01); *B01J 23/72* (2013.01); *B01J 23/755* (2013.01); *B01J 21/14* (2013.01); *C07C 29/149* (2013.01); *B01J 23/8892* (2013.01); *B01J 23/78* (2013.01); *B01J 23/80* (2013.01); *B01J 23/8872* (2013.01)

(58) Field of Classification Search
CPC ........... B01J 23/72; B01J 23/755; B01J 21/14
USPC ......... 502/241, 244, 245, 251, 252, 103, 104, 502/107, 117
See application file for complete search history.

(56) References Cited

U.S. PATENT DOCUMENTS 4,064,336 A * 12/1977 Hwang .................. 526/172
4,071,673 A *  1/1978 Hwang .................. 526/123.1

* cited by examiner

*Primary Examiner* — Elvis O Price
(74) *Attorney, Agent, or Firm* — Matthias Scholl P.C.; Matthias Scholl

(57) ABSTRACT

A catalyst including: a support, the support including a mixture of $SiO_2$ and $ZrO_2$; an active ingredient including copper; a first additive including a metal, an oxide thereof, or a combination thereof; and a second additive including Li, Na, K, or a combination thereof. The metal is Mg, Ca, Ba, Mn, Fe, Co, Zn, Mo, La, or Ce. Based on the total weight of the catalyst, the weight percentages of the different components are as follows: $SiO_2$=50-90 wt. %; $ZrO_2$=0.1-10 wt. %; copper=10-50 wt. %; the first additive=0.1-10 wt. %; and the second additive=0.1-5 wt. %.

20 Claims, 1 Drawing Sheet

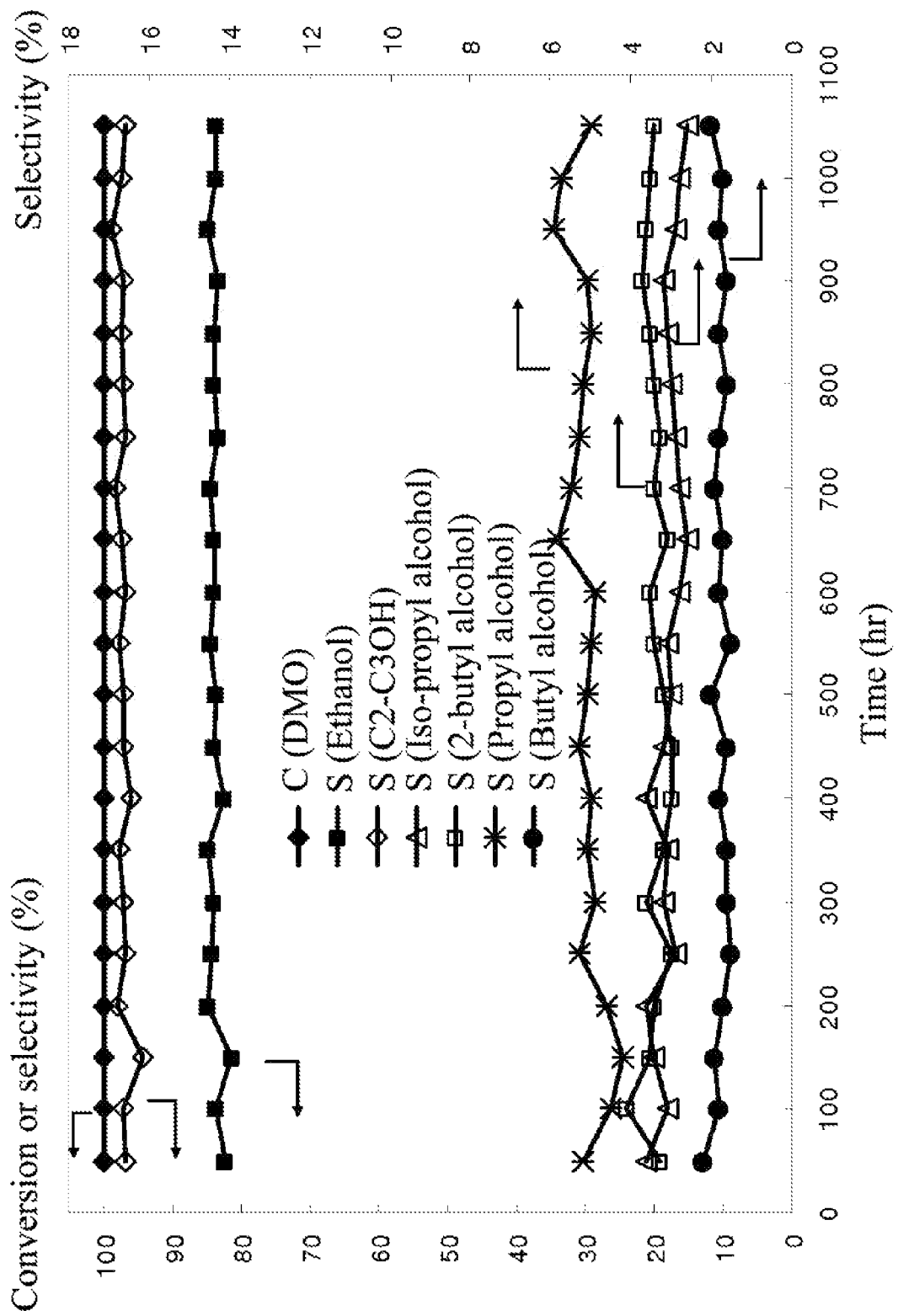

CATALYST FOR HYDROGENATION OF OXALIC ESTER TO ETHANOL, METHOD OF PREPARING THE CATALYST, AND METHOD OF USING THE SAME

CROSS-REFERENCE TO RELATED APPLICATIONS

This application is a continuation-in-part of International Patent Application No. PCT/CN2012/075110 with an international filing date of May 7, 2012, designating the United States, now pending, and further claims priority benefits to Chinese Patent Application No. 201110227292.9 filed Aug. 10, 2011. The contents of all of the aforementioned applications, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 14781 Memorial Drive, Suite 1319, Houston, Tex. 77079.

BACKGROUND OF THE INVENTION

1. Field of the Invention

The invention relates to a catalyst for hydrogenation of oxalic ester to ethanol, a method for preparing the catalyst and a method for using the same.

2. Description of the Related Art

Traditional technology for production of ethanol mainly includes ethylene hydration and biomass fermentation. Ethylene hydration route uses ethylene, a cracked product of petroleum, as raw material to yield ethanol by hydration of ethylene. Biological fermentation refers to the use of agricultural products which contain a variety of sugars (disaccharide), starches (polysaccharides), cellulose (hexose), forestry by-products and wild plants as raw materials. Polysaccharides and disaccharides are first hydrolyzed to yield monosaccharide and monosaccharide is then fermented to produce ethanol.

Due to resource conditions, the large-scale use of sugar or corn to produce fuel ethanol is limited and the technology with cellulose as the raw material to produce ethanol is not yet mature. Production of ethanol from synthesis gas has attracted great attention as synthesis gas can be acquired from coal, natural gas, or biomass resources. The production of ethanol from synthesis gas includes first preparing two carbon products such as acetaldehyde, ethanol, ethyl acetate and acetic acid over Rh/SiO$_2$ catalyst under 3-10 MPa and 300° C., and then the by-products such as acetaldehyde, ethyl acetate and acetic acid are further converted to ethanol through hydrogenation over Cu/SiO$_2$, Pd—Fe/SiO$_2$ or Cu—Zn—Al—Mg—Mo catalysts. Due to the rigorous technical conditions, poor stability and low selectivity of the catalyst, the method cannot be applied in large scale up to now.

Conventional copper-based catalysts for hydrogenation of acetate to ethanol have a low conversion rate and the reaction efficiency is quite low, and the stability data was not reported. The catalytic stability is critical for copper catalysts because metallic particles on the surface of catalyst are prone to aggregate and sinter at high temperature. Therefore, the development of copper-based catalyst with high resistance to sintering, high activity and selectivity at high temperature for hydrogenation of oxalic ester is one of the key technologies.

SUMMARY OF THE INVENTION

In view of the above-described problems, it is one objective of the invention to provide a catalyst for hydrogenation of oxalic ester to ethanol that has high degree of dispersion and good resistance to sintering at high temperature.

It is another objective of the invention to provide a method for preparing the catalyst that is capable of enhancing the interaction between copper and a support thereof and stabilizing the valence states of active sites and the particle sizes.

It is still another objective of the invention to provide a method for hydrogenation of oxalic ester to ethanol using the catalyst. The method can reduce the cost of production, improve the production capacity, and prolong the lifespan of the catalyst.

To achieve the above objectives, in accordance with one embodiment of the invention, there is provided a catalyst for hydrogenation of oxalate to ethanol, comprising a support comprising a mixture of SiO$_2$ and ZrO$_2$; an active ingredient comprising copper; a first additive comprising a metal, an oxide thereof, or a combination thereof, the metal being selected from the group consisting of Mg, Ca, Ba, Mn, Fe, Co, Zn, Mo, La, and Ce; and a second additive comprising Li, Na, K, or a combination thereof. Based on a total weight of the catalyst, weight percentages of different components are listed as follows: SiO$_2$=50-90 wt. %, ZrO$_2$=0.1-10 wt. %, copper=10-50 wt. %, the first additive=0.1-10 wt. %, and the second additive=0.1-5 wt. %.

In a class of this embodiment, silica accounts for 50-80 wt. % of the catalyst.

In a class of this embodiment, zirconia accounts for 0.5-4 wt. % of the catalyst.

In a class of this embodiment, copper accounts for 20-40 wt. % of the catalyst.

In a class of this embodiment, the first additive accounts for 0.5-5 wt. % of the catalyst.

In a class of this embodiment, the second additive accounts for 0.3-1 wt. % of the catalyst.

In accordance with another embodiment of the invention, there provided is a preparation method of the catalyst for hydrogenation of oxalate to ethanol, the preparation method comprising the steps of:

(1) providing an aqueous solution comprising a soluble copper precursor;

(2) providing a first soluble precursor comprising the first additive, and uniformly mixing the first soluble precursor with the soluble copper precursor;

(3) adding a precipitator of aqueous ammonia or urea to the aqueous solution and stirring;

(4) dissolving a precursor of Zr with diluted nitric acid and adding aqueous ammonia to the precursor until a pH value therein is 1.5-2.0 to form a semitransparent Zr sol;

(5) adding the Zr sol to gel sol and stirring for 2-10 h under heating;

(6) adding a mixed sol obtained in step 5) to the aqueous solution obtained in step 3), stirring for 2-12 h, heating the mixture to 50-100° C. to allow the precipitation of copper and the first additive, terminating heating when the pH value is lower than 7, filtering a resulting precipitant, washing, and drying; and (7) providing a second soluble precursor comprising the second additive, adding the second soluble precursor to the precipitant obtained in step 6, mixing, drying, and calcining.

In accordance with still another embodiment of the invention, there provided is a preparation method of the catalyst for hydrogenation of oxalate to ethanol, the preparation method comprising the steps of:

1) providing an aqueous solution comprising one or two soluble copper precursors, the aqueous solution comprising 0.2-2 M copper ions;

2) providing a first soluble precursor comprising the first additive, and uniformly mixing the first soluble precursor with the soluble copper precursor;

3) adding a precipitator of aqueous ammonia or urea to the aqueous solution and stirring until a pH value therein is 10-12;

4) dissolving a precursor of Zr with diluted nitric acid and adding aqueous ammonia to the precursor until a pH value therein is 1.5-2.0 to form a 0.1-3 mol/L Zr sol;

5) adding the Zr sol to gel sol and stirring for 2-10 h at 30-70° C.;

6) adding a mixed sol obtained in step 5) to the aqueous solution obtained in step 3), stirring for 2-12 h, heating the mixture to 50-100° C. to allow the precipitation of copper and the first additive, terminating heating when the pH value is lower than 7, filtering a resulting precipitant, washing trice with water, and drying for 2-24 h at 60-140° C.; and 7) providing a second soluble precursor comprising the second additive, adding the second soluble precursor to the precipitant obtained in step 6), mixing, standing for 0.5-12 h, drying for 2-24 h at 60-140° C., and calcining for 1-10 h at 200-600° C.

In a class of this embodiment, the soluble copper precursor is nitrate, chloride, or acetate.

In a class of this embodiment, the second soluble precursor is a nitrate, chloride, carbonate, bicarbonate, or hydroxide.

In a class of this embodiment, the precursor of Zr is $Zr(NO_3)_4$, $ZrO(NO_3)_2$, $ZrOCl_2$, $ZrO(OH)_2$, or a mixture thereof.

In a class of this embodiment, the first additive is a nitrate, chloride, or acetate of a metal selected from the group consisting of Mg, Ca, Ba, Mn, Fe, Co, Zn, Mo, La, Ce.

In a class of this embodiment, the second soluble precursor is $Li(NO_3)_2$ or KOH.

This invention further provides a method for producing ethanol by hydrogenation of an oxalate using the catalyst, the method comprising: shaping the catalyst and placing it in a fix-bed reactor for reduction in a 5-20% $H_2/N_2$ atmosphere at a temperature of 200-500° C. for 4-24 h; after reduction, filling the reactor with pure hydrogen and controlling a reaction temperature at between 240 and 300° C. and reaction pressure between 1 and 4 MPa, gasifying, preheating, and pumping 10-25 wt. % dimethyl oxalate (DMO) in methanol, liquid DMO, or diethyl oxalate (DEO) into the reactor to react with the hydrogen to produce EtOH and other low carbon alcohols.

In a class of this embodiment, a liquid hourly space velocity (LHSV) of oxalate is controlled at between 0.5 and 2 $h^{-1}$ and a molar ratio of $H_2/DMO$ is between 100 and 600.

In a class of this embodiment, the reaction temperature is 250-300° C.; the reaction pressure is between 2.0 and 4.0 MPa and the molar ratio of $H_2/DMO$ is between 200 and 500.

In this invention, a support comprising a mixture of $SiO_2$ and $ZrO_2$ is used. The specific surface area, the pore size distribution and the copper dispersion are improved by adding the first additive, while the second additive reinforces the resistance ability to sintering.

In the reaction of hydrogenation of dimethyl oxalate carried out by the catalyst mentioned in this invention, the reaction temperature is 280° C., pressure is 2.5 MPa, conversion of oxalate is 100%, selectivity of ethanol is as high as 85%, selectivity of low carbon alcohol (the sum of ethanol, isopropanol, propanol, butanol and 2-butanol) is higher than 97%, which presents high activity and selectivity.

BRIEF DESCRIPTION OF THE DRAWINGS

The invention is described hereinbelow with reference to accompanying drawings, in which the sole FIGURE is a schematic diagram of thermal stability date of a catalyst for hydrogenation of oxalic ester to produce ethanol according to one embodiment of the invention.

DETAILED DESCRIPTION OF THE EMBODIMENTS

This invention will be described in detail through following example more specifically, but not limit to these examples.

EXAMPLE 1

Preparation of Zirconium Sol 30 g of $Zr(NO_3)_4 \cdot 5H_2O$ was dissolved in 100 mL of 70% nitric acid in a 200 mL beaker and the concentration of $Zr(NO_3)_4$ was adjusted to 2M by adding deionized water. Ammonia aqueous solution was then added to the above solution until the pH reached 4.0-5.0 to obtain a semi-transparent zirconium sol, whose concentration was adjusted to 1M by adding deionized water. The above zirconium sol was aged for 24-48 h under stirring.

Preparation of the Catalyst 12.2 g of $Cu(NO_3)_2 \cdot 5H_2O$ and 3.1 g of $Mg(NO_3)_2$ were dissolved in 120 mL water. 32.9 mL of 25 wt. % ammonia aqueous solution was slowly added.

6.5 mL of zirconium sol as prepared and 31.6 mL of 30 wt. % silica sol were added to the above solution by drops and the solution was aged for 5 hours under stirring at 50° C. Then the sol was added to the copper ammonia complex solution and aged with stirring for another 4 hours. The temperature was raised to 80° C., and the heating was terminated until the pH was lower than 7 to allow for the precipitation of copper and silicate. The filtrate was washed with 200 mL of deionized water for 3 times, dried at 120° C. for 12 h. The catalyst was prepared by an incipient wetness method to impregnate powder with basic solution containing 0.4 g LiNO3. After 4 h of impregnation, the catalyst was dried for 12 hours at 120° C. and calcined at 450° C. for 4 hours to form $CuO$—$Li_2O/SiO_2$—$ZrO_2$—$MgO$ catalyst powder with CuO content of 20 wt. %, $SiO_2$ content of 71 wt. %, $ZrO_2$ content of 5 wt. %, MgO content of 3 wt. % and $Li_2O$ content of 1 wt. %.

Catalytic Test 0.8 g catalysts (40-60 meshes) were placed in a fixed bed reactor. The reaction test was carried out upon the reduction of catalyst in 20% $H_2/N_2$ atmosphere at 350° C. for 4 h, at a gas speed of 200 mL/min. Pure hydrogen was introduced into the system and the activity test was carried out at 270° C. and the pressure was controlled at 2.5 MPa after reduction. 20 wt. % of dimethyl oxalate in methanol was pumped into the system by liquid high pressure pump. The LHSV of dimethyl oxalate is 1 $h^{-1}$ and ratio of hydrogen to ester is 300. Sample was analyzed to calculate conversion and selectivity. The reaction products were condensed and analyzed on a GC 6820 equipped with a flame ionization detector (FID). Main by-products comprise propyl alcohol, butyl alcohol, methyl glycollate, and 1,2-butanediol. Result is displayed in table 1.

After 24 hours, stop feeding and raise the temperature to 400° C. in $N_2$ atmosphere for 24 h. Return to the previous reaction conditions and start reaction again. Result is displayed in Table 1.

TABLE 1

Activity data of hydrogenation of oxalate

| | | | | Selectivity, % | | | | |
|---|---|---|---|---|---|---|---|---|
| Example | Deterioration treatment | DMO/DEO Conversion, % | Ethanol | Isopropyl alcohol | 2-butyl alcohol | Propyl alcohol | Butyl alcohol | $C_2$-$C_3$ OH |
| Example 1 | before | 100 | 72.6 | 5.8 | 11.7 | 3.7 | 3 | 96.8 |
| | after | 100 | 72.5 | 5.9 | 11.2 | 3.8 | 2.8 | 96.2 |
| Comparative Example 1 | before | 100 | 67.8 | 4.7 | 15.8 | 3.9 | 3.5 | 95.6 |
| | after | 100 | 63.2 | 5.5 | 16.5 | 3.3 | 3.0 | 91.5 |
| Example 2 | before | 100 | 79.8 | 4 | 8.6 | 2.1 | 2.2 | 96.7 |
| | after | 100 | 79.5 | 3.3 | 9.2 | 2.5 | 2.2 | 96.7 |
| Example 3 | before | 100 | 85.1 | 2.8 | 4.8 | 1.8 | 2.7 | 97.2 |
| | after | 100 | 84.2 | 2.2 | 5.5 | 1.6 | 2.2 | 95.7 |
| Example 4 | before | 100 | 75.4 | 10.9 | 2.4 | 2.6 | 1.5 | 92.8 |
| | after | 100 | 74.9 | 8.5 | 5 | 2.9 | 1.8 | 93.1 |
| Example 5 | before | 100 | 67.3 | 0 | 19.3 | 4.3 | 4.2 | 95.1 |
| | after | 100 | 67.2 | 0 | 20.2 | 3.8 | 4.5 | 95.7 |
| Example 6 | before | 100 | 75.4 | 3.8 | 10.2 | 1.9 | 2.3 | 93.6 |
| | after | 100 | 74.3 | 3.2 | 11.4 | 2 | 1.9 | 92.8 |
| Example 7 | before | 99.9 | 78.3 | 0 | 13.2 | 0 | 5.2 | 96.7 |
| | after | 99.8 | 77.8 | 0 | 14.2 | 0 | 4.8 | 96.8 |
| Example 8 | before | 100 | 83.7 | 3 | 3.5 | 5.2 | 1.8 | 97.2 |

COMPARATIVE EXAMPLE 1

Preparation of Zirconium Sol

Preparation of Zirconium sol is the same as in Example 1.
Preparation of Catalyst 12.2 g of $Cu(NO_3)_2 \cdot 5H_2O$ was dissolved in water. 32.9 mL of 25 wt. % ammonia aqueous solution was slowly added.

6.5 mL of the zirconium sol as prepared and 33.3 mL of 30 wt. % silica sol was added to the above solution by drops and aged for 5 h under stirring at 50° C. Then the sol was added to the copper ammonia complex solution and aged by stirring for another 4 h. The temperature was raised to 80° C. When the pH was lower than 7, stop heating and allow for the precipitate of copper and silicate. The filtrate was washed with 200 mL of deionized water for 3 times, dried at 120° C. for 12 h, calcined at 450° C. for 4 h to form $CuO/SiO_2$—$ZrO_2$ catalyst powder with Cu content of 20 wt. %, $SiO_2$ content of 75 wt. %, $ZrO_2$ content of 5 wt. %.

Catalytic Test

Catalytic activity test was carried out in the same way described in Example 1.

Result was in Table 1.

EXAMPLE 2

Preparation of Zirconium Sol

Preparation of Zirconium sol is the same as in Example 1.
Preparation of Catalysts 18.2 g of $Cu(NO_3)_2 \cdot 5H_2O$ and 0.7 g of $Mg(OH)_2$ was dissolved in 150 mL water. 49.3 mL of 25 wt. % ammonia aqueous solution was slowly added to form the aqueous solution A. 6.5 mL of zirconium sol as prepared and 27.1 mL of 30 wt. % silica sol was added to the solution A by drops and aged for 5 h under stirring at 50° C. Then the sol was added to the copper ammonia complex solution and aged by stirring for another 4 h. The temperature was raised to 80° C., till the pH was lower than 7, the heating was terminated, allow for the precipitate of copper and silicate. The filtrate was washed with 200 mL of deionized water for 3 times, dried at 120° C. for 12 h. The catalyst was prepared by an incipient wetness method to impregnate powder with basic solution containing 0.4 g $LiNO_3$. After 4 h of impregnation, dry the catalyst for 12 h at 120° C., calcine at 450° C. for 4 h to form $CuO$—$Li_2O/SiO_2$—$ZrO_2$—$MgO$ catalyst powder with CuO content of 30 wt. %, $SiO_2$ content of 61 wt. %, $ZrO_2$ content of 5 wt. %, MgO content of 3 wt. %, $Li_2O$ content of 1 wt. %.

Catalytic Test 0.8 g catalysts (40-60 meshes) were placed in a fixed bed reactor. The reaction test was carried out upon the reduction of catalyst in 20% $H_2/N_2$ atmosphere at 400° C. for 4 h, at a gas flow speed of 200 mL/min. Pure hydrogen was introduced into the system and activity test was carried out at 280° C. and the pressure was controlled at 2.5 MPa after reduction. 20 wt. % of dimethyl oxalate in methanol was pumped into the system by liquid high pressure pump. The LHSV of dimethyl oxalate is 0.75 $h^{-1}$, ratio of hydrogen to ester is 400. Sample was analyzed to calculate conversion and selection. The reaction products were condensed and analyzed on a GC 6820 equipped with a flame ionization detector (FID). Main by-products include propyl alcohol, butyl alcohol, methyl glycollate, and 1,2-butanediol. Result is displayed in Table 1.

After 24 hours, stop feeding, and raise the temperature to 400° C. in $N_2$ atmosphere for 24 h. Return to the previous reaction conditions, and start reaction again. Result is displayed in table 1.

EXAMPLE 3

Preparation of Zirconium Sol

Preparation of Zirconium sol is the same as Example 1.
Preparation of Catalyst 24.3 g of $Cu(NO_3)_2 \cdot 5H_2O$ and 1.1 g of $Ba(NO)_3$ was dissolved in 200 mL water. 65.8 mL of 25 wt. % ammonia aqueous solution was slowly added to form the aqueous solution A. 6.5 mL of zirconium sol as prepared and 20 mL of 30 wt. % silica sol was added to the solution A by drops and aged for 5 h under stirring at 50° C. Then the sol was added to the copper ammonia complex solution and aged by stirring for another 4 h. The temperature was raised to 80° C., till the pH was lower than 7, the heating was terminated, allow for the precipitate of copper and silicate. The filtrate was washed with 200 mL of deionized water for 3 times, dried at 120° C. for 12 h. The catalyst was prepared by an incipient wetness method to impregnate powder with basic solution containing 0.1 g KOH. After 4 h of impregnation, dry the catalyst for 12 h at 120° C., calcined at 450° C. for 4 h to form CuO—K$_2$O/SiO$_2$—ZrO$_2$—BaO catalyst powder with CuO content of 40 wt. %, SiO$_2$ content of 50 wt. %, ZrO$_2$ content of 5 wt. %, BaO content of 4 wt. %, K$_2$O content of 1 wt. %.

Catalytic Test 0.8 g catalysts (40-60 meshes) were placed in a fixed bed reactor. The reaction test was carried out upon the reduction of catalyst in 20% H$_2$/N$_2$ atmosphere at 400° C. for 4 h, at a gas flow speed of 200 mL/min. Pure hydrogen was allowed into the system, performance was tested at 280° C. and the pressure was controlled at 4 MPa after reduction. 20 wt. % of dimethyl oxalate in methanol went through the system by liquid high pressure pump. The LHSV of dimethyl oxalate is 1.5 h$^{-1}$, hydrogen ester ratio is 600. Sample was analyzed to calculate conversion and selection. The reaction products were condensed and analyzed on a GC 6820 equipped with a flame ionization detector (FID). Main by-products include propyl alcohol, butyl alcohol, methyl glycollate, and 1,2-butanediol. Result is displayed in Table 1.

After 24 hours, stop feeding, and raise the temperature to 400° C. in N$_2$ atmosphere for 24 h. Return to the previous reaction conditions, and start reaction again. Result is displayed in table 1.

EXAMPLE 4

Preparation of Zirconium Sol

Preparation of Zirconium sol is the same as in Example 1.

Preparation of Catalysts 18.2 g of Cu(NO$_3$)$_2$.5H$_2$O and 0.2 g of Fe(NO$_3$)$_3$.9H$_2$O was dissolved in 150 mL water. 49.3 mL of 25 wt. % ammonia aqueous solution was slowly added to form the aqueous solution A. 2.6 mL of zirconium sol prepared and 29.8 mL of 30 wt. % silica sol was added to the solution A by drop and aged for 5 h under stirring at 30° C. Then the sol was added to the copper ammonia complex solution and aged by stirring for another 12 h. The temperature was raised to 70° C., till the pH was lower than 7, the heating was terminated, allow for the precipitate of copper and silicate. The filtrate was washed with 200 mL of deionized water for 3 times, dried at 140° C. for 6 h. The catalyst was prepared by an incipient wetness method to impregnate powder with basic solution containing 0.2 g LiNO$_3$. After 4 h of impregnation, dry the catalyst for 6 h at 140° C., calcine at 450° C. for 8 h to form CuO—Li$_2$O/SiO$_2$—ZrO$_2$—Fe$_2$O$_3$ catalyst powder with CuO content of 30 wt. %, SiO$_2$ content of 67 wt. %, ZrO$_2$ content of 2 wt. %, Fe$_2$O$_3$ content of 0.5 wt. %, Li$_2$O content of 0.5 wt. %.

Catalytic Test 0.8 g catalysts (40-60 meshes) were placed in A fixed bed reactor. The reaction test was carried out upon the reduction of catalyst in 20% H$_2$/N$_2$ atmosphere at 350° C. for 12 h, at a gas flow speed of 200 mL/min. Pure hydrogen was allowed into the system, performance was tested at 280° C. and the pressure was controlled at 3 MPa after reduction. 20 wt. % of dimethyl oxalate in methanol went through the system by liquid high pressure pump. The LHSV of dimethyl oxalate is 1 h$^{-1}$, hydrogen ester ratio is 600. Sample was analyzed to calculate conversion and selection. The reaction products were condensed and analyzed on a GC 6820 equipped with a flame ionization detector (FID). Main by-products include propyl alcohol, butyl alcohol, methyl glycollate, and 1,2-butanediol. Result is displayed in Table 1.

After 24 hours, stop feeding, and raise the temperature to 400° C. in N$_2$ atmosphere for 24 h. Return to the previous reaction conditions, and start reaction again. Result is displayed in table 1.

EXAMPLE 5

Preparation of Zirconium Sol

Preparation of Zirconium sol is the same as in Example 1.

Preparation of Catalysts 18.2 g of Cu(NO$_3$)$_2$.5H$_2$O and 1.1 g of La(NO$_3$)$_3$.6(H$_2$O) was dissolved in 150 mL water. 49.3 mL of 25 wt. % ammonia aqueous solution was slowly added to form the aqueous solution A. 1.3 mL of zirconium sol prepared and 28.2 mL of 30 wt. % silica sol was added to the solution A by drop and aged for 5 h under stirring at 30° C. Then the sol was added to the copper ammonia complex solution and aged by stirring for another 12 h. The temperature was raised to 80° C., till the pH was lower than 7, the heating was terminated, allow for the precipitate of copper and silicate. The filtrate was washed with 200 mL of deionized water for 3 times, dried at 120° C. for 12 h. The catalyst was prepared by an incipient wetness method to impregnate powder with basic solution containing 0.2 g LiNO$_3$. After 4 h of impregnation, dry the catalyst for 6 h at 140° C., calcine at 450° C. for 8 h to form CuO—Li$_2$O/SiO$_2$—ZrO$_2$—La$_2$O$_3$ catalyst powder with CuO content of 30 wt. %, SiO$_2$ content of 63.5 wt. %, ZrO$_2$ content of 1 wt. %, La$_2$O$_3$ content of 5 wt. %, Li$_2$O content of 0.5 wt. %.

Catalytic Test 0.8 g catalysts (40-60 meshes) were placed in a fixed bed reactor. The reaction test was carried out upon the reduction of catalyst in 20% H$_2$/N$_2$ atmosphere at 350° C. for 12 h, with a gas flow speed of 200 mL/min. Pure hydrogen was allowed into the system, performance was tested at 250° C. and the pressure was controlled at 2.5 MPa after reduction. 20 wt. % of dimethyl oxalate in methanol went through the system by liquid high pressure pump. The LHSV of dimethyl oxalate is 0.5 h$^{-1}$, hydrogen ester ratio is 300. Sample was analyzed to calculate conversion and selection. The reaction products were condensed and analyzed on a GC 6820 equipped with a flame ionization detector (FID). Main by-products include propyl alcohol, butyl alcohol, methyl glycollate, and 1,2-butanediol. Result is displayed in Table 1.

After 24 hours, stop feeding, and raise the temperature to 400° C. in N$_2$ atmosphere for 24 h. Return to the previous reaction conditions, and start reaction again. Result is displayed in table 1.

EXAMPLE 6

Preparation of Zirconium Sol

Preparation of Zirconium sol is the same as in Example 1.

Preparation of Catalysts 18.2 g of Cu(NO$_3$)$_2$.5H$_2$O and 1.1 g of Zn(NO$_3$)$_3$.6(H$_2$O) was dissolved in 150 mL water. 49.3 mL of 25 wt. % ammonia aqueous solution was slowly added to form the aqueous solution A. 0.5 mL of zirconium sol prepared and 28.6 mL of 30 wt. % silica sol was added to the solution A by drop and aged for 5 h under stirring at 30° C. Then the sol was added to the copper ammonia complex solution and aged by stirring for another 12 h. The temperature was raised to 80° C., till the pH was lower than 7, the heating was terminated, allow for the precipitate of copper and silicate. The filtrate was washed with deionized water for 3 times, dried at 120° C. for 12 h. The catalyst was prepared by an incipient wetness method to impregnate powder with basic solution containing 0.2 g LiNO$_3$. After 4 h of impregnation, dry the catalyst for 6 h at 140° C., calcine at 450° C. for 8 h to form CuO—Li$_2$O/SiO$_2$—ZrO$_2$—ZnO catalyst powder with CuO content of 30 wt. %, SiO$_2$ content of 64.3 wt. %, ZrO$_2$ content of 0.4 wt. %, ZnO content of 5 wt. %, Li$_2$O content of 0.3 wt. %.

Catalytic Test 0.8 g catalysts (40-60 meshes) were placed in a fixed bed reactor. The reaction test was carried out upon the reduction of catalyst in 20% H$_2$/N$_2$ atmosphere at 400° C. for 16 h, with a gas flow speed of 200 mL/min. Pure hydrogen was allowed into the system, performance was tested at 280° C. and the pressure was controlled at 2.5 MPa after reduction. 20 wt. % of dimethyl oxalate in methanol went through the system by liquid high pressure pump. The LHSV of dimethyl oxalate is 1.25 h$^{-1}$, hydrogen ester ratio is 300. Sample was analyzed to calculate conversion and selection. The reaction products were condensed and analyzed on a GC equipped with a flame ionization detector (FID). Main by-products include propyl alcohol, butyl alcohol, methyl glycollate, and 1,2-butanediol. Result is displayed in Table 1.

After 24 hours, stop feeding, and raise the temperature to 400° C. in N$_2$ atmosphere for 24 h. Return to the previous reaction conditions, and start reaction again. Result is displayed in table 1.

EXAMPLE 7

Except for using diethyl oxalate as raw materials instead of 20 wt. % dimethyl oxalate methanol solution as well as 300° C. of reaction temperature, others procedures are the same as in Example 1. Result is displayed in Table 1.

EXAMPLE 8

Preparation of Zirconium Sol

Preparation of Zirconium sol is the same as in Example 1.

Preparation of Catalysts 243.2 g of Cu(NO$_3$)$_2$.5H$_2$O and 30.5 g of Mg(NO$_3$)$_2$ was dissolved in 1500 mL water. 657.6 mL of 25 wt. % ammonia aqueous solution was slowly added to form the aqueous solution A. 65.0 mL of zirconium sol as prepared and 226.7 mL of 30 wt. % silica sol was added to the solution A by drops and aged for 5 h under stirring at 50° C. Then the sol was added to the copper ammonia complex solution and aged by stirring for another 6 h. The temperature was raised to 80° C., till the pH was lower than 7, the heating was terminated, allow for the precipitate of copper and silicate. The filtrate was washed with 200 mL of deionized water for 3 times, dried at 120° C. for 12 h. The catalyst was prepared by a incipient wetness method to impregnate powder with basic solution containing 3.7 g LiNO$_3$. After 4 h of impregnation, dry the catalyst for 6 h at 120° C. and calcined at 450° C. for 4 h to form CuO—Li$_2$O/SiO$_2$—ZrO$_2$—MgO catalyst powder with CuO content of 40 wt. %, SiO$_2$ content of 51 wt. %, ZrO$_2$ content of 5 wt. %, MgO content of 3 wt. %, Li$_2$O content of 1 wt. %.

Catalytic Test 300 mL tabletting catalysts (Φ3*3) were placed in a fixed bed reactor (32 mm internal diameter). The reaction test was carried out upon the reduction of catalyst in 20% H$_2$/N$_2$ atmosphere (1500 L/h) at 350° C. for 24 h. Pure hydrogen was introduced into the system and activity test was carried out at 280° C. and the pressure was controlled at 3 MPa after reduction. Molten liquid phase dimethyl oxalate was pumped into the system by heat preservation liquid high pressure pump. The LHSV of dimethyl oxalate is 1.25 h$^{-1}$, ratio of hydrogen to ester is 400. Sample was analyzed to calculate conversion and selection. Sample was analyzed to calculate conversion and selection. The reaction products were condensed and analyzed on a GC equipped with a flame ionization detector (FID). Main by-products include propyl alcohol, butyl alcohol, methyl glycollate, and 1,2-butanediol. Result is displayed in Table 1.

The invention claimed is:

1. A catalyst, comprising:
    a) a support comprising a mixture of SiO$_2$ and ZrO$_2$;
    b) an active ingredient comprising copper;
    c) a first additive comprising a metal, an oxide thereof, or a combination thereof, the metal being selected from the group consisting of Mg, Ca, Ba, Mn, Fe, Co, Zn, Mo, La, and Ce; and
    d) a second additive comprising Li, Na, K, or a combination thereof;
    wherein based on a total weight of the catalyst, the following components are provided in the following weigh percentages:
    SiO$_2$=50-90 wt. %;
    ZrO$_2$=0.1-10 wt. %;
    copper=10-50 wt. %;
    the first additive=0.1-10 wt. %; and
    the second additive=0.1-5 wt. %.

2. The catalyst of claim 1, wherein the weight of SiO$_2$ is 50-80% of that of the catalyst.

3. The catalyst of claim 1, wherein the weight of ZrO$_2$ is 0.4-5% of that of the catalyst.

4. The catalyst of claim 1, wherein the weight of active ingredient copper is 20-40% of that of the catalyst.

5. The catalyst of claim 1, wherein the weight of first additive is 0.5-5% of that of the catalyst.

6. The catalyst of claim 1, wherein the weight of second additive is 0.3-1% of that of the catalyst.

7. A method for preparing the catalyst of claim 1, the method comprising:
    1) providing an aqueous solution comprising a soluble copper precursor;
    2) providing a first soluble precursor comprising the first additive, and uniformly mixing the first soluble precursor with the soluble copper precursor;
    3) adding a precipitator of aqueous ammonia or urea to the aqueous solution and stirring;
    4) dissolving a precursor of Zr with diluted nitric acid and adding aqueous ammonia to the precursor until a pH value therein is 1.5-2.0 to form a semitransparent Zr sol;
    5) adding the Zr sol to gel sol and stirring for 2-10 h under heating;
    6) adding a mixed sol obtained in step 5) to the aqueous solution obtained in step 3), stirring for 2-12 h, heating the mixture to 50-100° C. to allow for precipitation of copper and the first additive, terminating heating when the pH value is lower than 7, filtering a resulting precipitant, washing, and drying; and
    7) providing a second soluble precursor comprising the second additive, adding the second soluble precursor to the precipitant obtained in step 6, mixing, drying, and calcining.

8. The method of claim 7, wherein the soluble copper precursor is nitrate, chloride, or acetate.

9. The method of claim 7, wherein the second soluble precursor is nitrate, chloride, carbonate, bicarbonate, or hydroxide.

10. The method of claim 7, wherein the precursor of Zr is Zr(NO$_3$)$_4$, ZrO(NO$_3$)$_2$, ZrOCl$_2$, ZrO(OH)$_2$, or a mixture thereof.

11. The method of claim 7, wherein the first additive is a nitrate, a chloride, or a acetate of a metal selected from the group consisting of Mg, Ca, Ba, Mn, Fe, Co, Zn, Mo, La, Ce.

12. A method for preparing the catalyst of claim 1, the method comprising:
   1) providing an aqueous solution comprising one or two soluble copper precursors, the aqueous solution comprising 0.2-2 M copper ions;
   2) providing a first soluble precursor comprising the first additive, and uniformly mixing the first soluble precursor with the soluble copper precursor;
   3) adding a precipitator of aqueous ammonia or urea to the aqueous solution and stirring until a pH value therein is 10-12;
   4) dissolving a precursor of Zr with diluted nitric acid and adding aqueous ammonia to the precursor until a pH value therein is 1.5-2.0 to form a 0.1-3 mol/L Zr sol;
   5) adding the Zr sol to gel sol and stirring for 2-10 h at 30-70° C.;
   6) adding a mixed sol obtained in step 5) to the aqueous solution obtained in step 3), stirring for 2-12 h, heating the mixture to 50-100° C. to allow for precipitation of copper and the first additive, terminating heating when the pH value is lower than 7, filtering a resulting precipitant, washing trice with water, and drying for 2-24 h at 60-140° C.; and
   7) providing a second soluble precursor comprising the second additive, adding the second soluble precursor to precipitant obtained in step 6), mixing, standing for 0.5-12 h, drying for 2-24 h at 60-140° C., and calcining for 1-10 h at 200-600° C.

13. The method of claim 12, wherein the soluble copper precursor is nitrate, chloride, or acetate.

14. The method of claim 12, wherein the second soluble precursor is nitrate, chloride, carbonate, bicarbonate, or hydroxide.

15. The method of claim 12, wherein the precursor of Zr is $Zr(NO_3)_4$, $ZrO(NO_3)_2$, $ZrOCl_2$, $ZrO(OH)_2$, or a mixture thereof.

16. The method of claim 12, wherein the first additive is a nitrate, a chloride, or a acetate of a metal selected from the group consisting of Mg, Ca, Ba, Mn, Fe, Co, Zn, Mo, La, Ce.

17. The method of claim 12, wherein the second soluble precursor is $Li(NO_3)_2$ or KOH.

18. A method for producing ethanol by hydrogenation of an oxalate using the catalyst of claim 1, the method comprising: shaping the catalyst and placing in a fix-bed reactor for reduction in a 5-20% $H_2/N_2$ atmosphere at a temperature of 200-500° C. for 4-24 h; after reduction, filling the reactor with pure hydrogen and controlling a reaction temperature at between 240 and 300° C. and reaction pressure between 1 and 4 MPa, gasifying, preheating, and pumping 10-25 wt. % dimethyl oxalate (DMO) in methanol, liquid DMO, or diethyl oxalate (DEO) into the reactor to react with the hydrogen to produce EtOH and other low carbon alcohols.

19. The method of claim 18, wherein a liquid hourly space velocity (LHSV) of oxalate is controlled at between 0.5 and 2 $h^{-1}$ and a molar ratio of $H_2$/DMO is between 100 and 600.

20. The method of claim 18, wherein the reaction temperature is 250-300° C.; the reaction pressure is between 2.0 and 4.0 MPa and the molar ratio of $H_2$/DMO is between 200 and 500.

* * * * *